(12) United States Patent
Sato

(10) Patent No.: US 9,516,994 B2
(45) Date of Patent: Dec. 13, 2016

(54) BALLOON DETACHMENT TOOL

(71) Applicant: OLYMPUS CORPORATION, Tokyo (JP)

(72) Inventor: Sunao Sato, Yamato (JP)

(73) Assignee: OLYMPUS CORPORATION, Tokyo (JP)

(\*) Notice: Subject to any disclaimer, the term of this patent is extended or adjusted under 35 U.S.C. 154(b) by 0 days.

(21) Appl. No.: 14/932,052

(22) Filed: Nov. 4, 2015

(65) Prior Publication Data

US 2016/0051129 A1 Feb. 25, 2016

Related U.S. Application Data

(63) Continuation of application No. PCT/JP2014/079870, filed on Nov. 11, 2014.

(30) Foreign Application Priority Data

Nov. 26, 2013 (JP) ................. 2013-244036

(51) Int. Cl.
| | | |
|---|---|---|
| *B23P 19/02* | (2006.01) | |
| *A61B 1/00* | (2006.01) | |
| *A61B 8/12* | (2006.01) | |
| *A61B 8/00* | (2006.01) | |
| *A61B 8/08* | (2006.01) | |

(52) U.S. Cl.
CPC ....... *A61B 1/00131* (2013.01); *A61B 1/00163* (2013.01); *A61B 8/0841* (2013.01); *A61B 8/12* (2013.01); *A61B 8/42* (2013.01); *A61B 8/4281* (2013.01); *A61B 8/4494* (2013.01); *A61B 8/00* (2013.01); *A61B 8/08* (2013.01)

(58) Field of Classification Search
USPC .......................................................... 29/235
See application file for complete search history.

(56) References Cited

U.S. PATENT DOCUMENTS 4,399,602 A \* 8/1983 Hancock ............ B23D 57/0015
174/10
5,062,193 A \* 11/1991 Thompson ............ B23P 11/022
29/235

(Continued)

FOREIGN PATENT DOCUMENTS

EP 1541080 A1 6/2005
JP H3-91312 U 9/1991

(Continued)

OTHER PUBLICATIONS

International Search Report dated Dec. 9, 2014 issued in PCT/JP2014/079870.

(Continued)

*Primary Examiner* — Alvin Grant
(74) *Attorney, Agent, or Firm* — Scully, Scott, Murphy & Presser, P.C.

(57) ABSTRACT

Included are a cylindrical holding portion, a groove engageable with a balloon band removed from a balloon engagement groove provided in an outer periphery of an ultrasound transducer unit, a cut portion provided in the holding portion, the cut portion allowing the holding portion to radially expand in a radial direction, and an abutment portion provided on a second opening side relative to the groove on an inner peripheral face of the holding portion.

7 Claims, 10 Drawing Sheets

(56) References Cited

U.S. PATENT DOCUMENTS

| | | | | |
|---|---|---|---|---|
| 5,068,953 A * | 12/1991 | Semotiuk | ................ | B25B 27/10 29/235 |
| 5,216,793 A * | 6/1993 | Semotiuk | ................ | B25B 27/10 29/235 |
| 5,216,954 A * | 6/1993 | Thompson | ............ | B41F 27/105 101/375 |
| 5,495,650 A * | 3/1996 | Crepel | ..................... | H02G 1/14 29/235 |
| 5,749,136 A * | 5/1998 | Bodiford | ................ | A47G 23/02 29/235 |
| 5,970,596 A * | 10/1999 | Cardinaels | ............... | H02G 1/14 29/235 |
| 6,415,488 B1 * | 7/2002 | Muto | ................... | B21D 39/048 29/222 |
| 6,450,931 B1 * | 9/2002 | Frey | ..................... | A43D 100/14 29/235 |
| 6,539,599 B2 * | 4/2003 | Martin | ..................... | B25B 27/28 269/48.1 |
| 6,775,891 B1 * | 8/2004 | Tsiguloff | ................ | B25B 27/28 29/235 |
| 7,467,457 B2 * | 12/2008 | Sorvino | .................. | F28F 13/00 174/252 |
| 8,364,280 B2 * | 1/2013 | Marnfeldt | .......... | A61B 17/3417 607/116 |
| 9,119,532 B2 * | 9/2015 | Terliuc | ............... | A61B 1/00131 |
| 2005/0125005 A1 | 6/2005 | Fujikura | | |
| 2007/0244361 A1 * | 10/2007 | Ikeda | .................. | A61B 1/00082 600/116 |

FOREIGN PATENT DOCUMENTS

| | | |
|---|---|---|
| JP | H08-173424 A | 7/1996 |
| JP | H08-182677 A | 7/1996 |
| JP | 2005-137413 A | 6/2005 |
| JP | 2005-193000 A | 7/2005 |
| JP | 2008-099745 A | 5/2008 |

OTHER PUBLICATIONS

Extended Supplementary European Search Report dated Oct. 10, 2016 in related European Application No. 14 86 5969.1.

* cited by examiner

BALLOON DETACHMENT TOOL

CROSS REFERENCE TO RELATED APPLICATION

This application is a continuation application of PCT/JP2014/079870 filed on Nov. 11, 2014 and claims benefit of Japanese Application No. 2013-244036 filed in Japan on Nov. 26, 2013, the entire contents of which are incorporated herein by this reference.

BACKGROUND OF INVENTION

1. Field of the Invention

The present invention relates to a balloon detachment tool for detaching a balloon from an outer periphery of an ultrasound transducer unit in a distal end of an insertion portion of an ultrasound endoscope.

2. Description of the Related Art

Ultrasound endoscopes that obtain an ultrasound image of a site to be examined by transmitting/receiving ultrasound to/from the site to be examined, from an ultrasound transducer inside an ultrasound transducer unit in a distal end of an insertion portion are publicly known.

Also, a configuration in which a balloon is attached to an outer periphery of the ultrasound transducer unit in order to efficiently transmit/receive ultrasound to/from the site to be examined and maintain a proper distance between the ultrasound transducer unit and the site to be examined is also publicly known. Note that an ultrasound transmission medium such as degassed water is enclosed in the balloon.

Also, the balloon is generally configured so that respective circumferential balloon bands provided at one end and the other end of the balloon are engaged in respective circumferential grooves formed on the distal-end side and the proximal-end side of the outer periphery of the ultrasound transducer unit, whereby the balloon is attached to the outer periphery of the ultrasound transducer unit.

Japanese Patent Application Laid-Open Publication No. 8-182677 discloses a balloon attachment apparatus that makes it easy to attach a balloon to an outer periphery of an ultrasound transducer unit.

More specifically, in the balloon attachment apparatus in Japanese Patent Application Laid-Open Publication No. 8-182677, a groove engageable with the balloon band at the other end of the balloon is formed in an outer periphery on the proximal-end side of a cap in which an ultrasound transducer unit can be loosely fitted.

A worker engages a balloon band at one end of a balloon in a groove on the distal-end side of an ultrasound transducer unit, and then, engages a balloon band at the other end of the balloon in a groove in an outer periphery of a cap.

Subsequently, the worker fits the ultrasound transducer unit into the cap, and lastly, moves the balloon band at the other end of the balloon from the groove in the outer periphery of the cap to the groove on the proximal-end side of the ultrasound transducer unit and is engaged in the groove on the proximal-end side of the ultrasound transducer unit by fingers, whereby the balloon can easily be attached to the outer periphery of the ultrasound transducer unit.

After the end of ultrasound observation, when the balloon is detached from the outer periphery of the ultrasound transducer unit, it is common that a worker performs the work of detaching the balloon while stroking the balloon with fingers with a rubber globe on via, e.g., a piece of gauze from the perspective of hygiene.

Here, it is conceivable that a balloon is detached using the balloon attachment apparatus disclosed in Japanese Patent Application Laid-Open Publication No. 8-182677.

More specifically, the balloon may be detached easily by, after an ultrasound transducer unit is fitted in the cap, moving a balloon band at the other end of the balloon, the balloon band being engaged in the groove on the proximal end of the ultrasound transducer unit, to the groove on the outer periphery of the cap and engaging the balloon band in the groove by, e.g., a sharp tool or fingers and subsequently extracting the cap.

SUMMARY OF THE INVENTION

A balloon detachment tool according to an aspect of the present invention includes: a cylindrical holding portion including a first opening on one end side in an axial direction, the first opening having an inner diameter that allows an ultrasound transducer unit in a distal end of an insertion portion of an ultrasound endoscope to be inserted and extracted, and a second opening on another end side in the axial direction; a groove formed at a position a set distance away toward the other end side in the axial direction from the one end in an outer periphery of the holding portion, the groove being engageable with an end portion of the balloon which is removed from a balloon engagement groove provided in an outer periphery of the ultrasound transducer unit; a cut portion provided in the holding portion, the cut portion allowing the holding portion to radially expand in a radial direction; and an abutment portion provided on an inner peripheral face of the holding portion and on the second opening side relative to the groove in the axial direction, the abutment portion positioning the groove so that the groove is located on a distal end side of the insertion portion of the ultrasound endoscope relative to the balloon engaging groove when the abutment portion is brought into abutment with the distal end of the insertion portion of the ultrasound endoscope.

DETAILED DESCRIPTION OF THE PREFERRED EMBODIMENT(S)

An embodiment of the present invention will be described with reference to the drawings. It should be noted that the drawings are schematic ones and, e.g., relationships between a thickness and a width of each member and ratios in thickness between the respective members are different from actual ones, and it should be noted that the drawings include parts that are different in dimensional relationships and/or ratios from one another.

Figure 1:
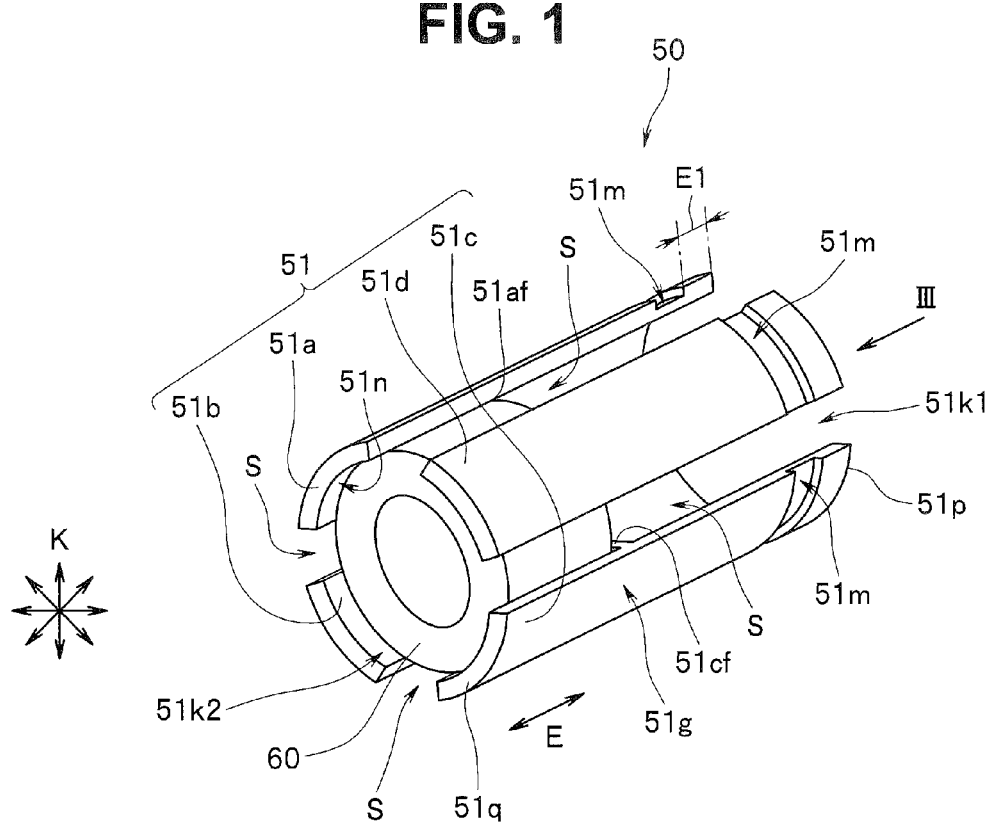
FIG. 1 is a perspective diagram illustrating a balloon detachment tool according to the present embodiment.
Figure 2:
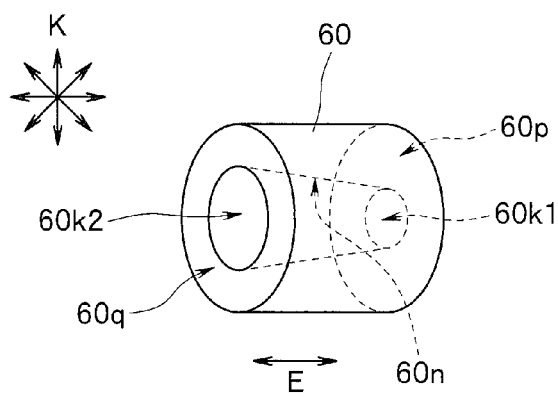
FIG. 2 is a perspective diagram illustrating the fitting portion in FIG. 1.
Figure 3:
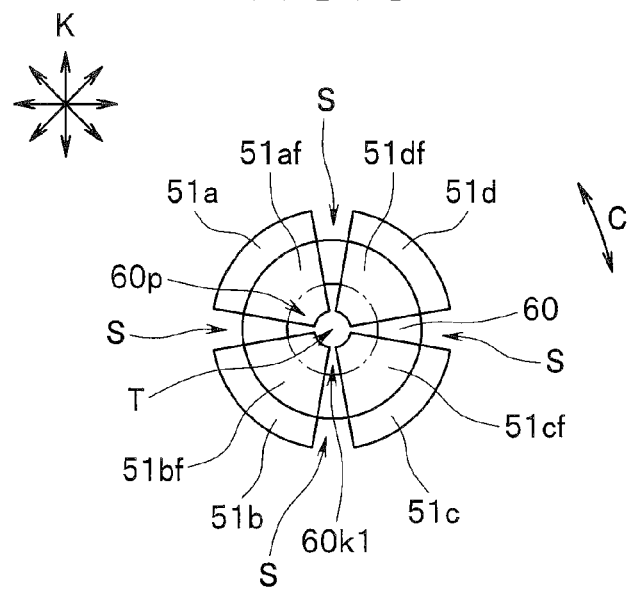
FIG. 3 is a back view of the balloon detachment tool in FIG. 1 as viewed in the III direction in FIG. 1.
Figure 4:
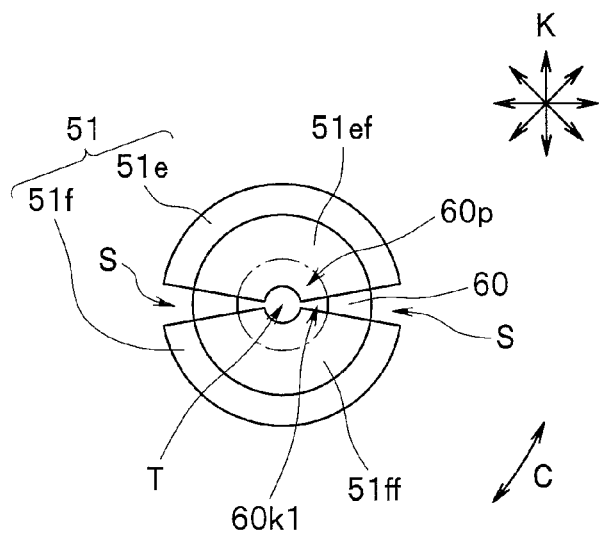
FIG. 4 is a back view of a balloon detachment tool, which indicates a modification in which two cut portions are formed in the holding portion in FIG. 1.

FIG. 1 is a perspective diagram illustrating a balloon detachment tool according to the present embodiment, FIG. 2 is a perspective diagram illustrating the fitting portion in FIG. 1, FIG. 3 is a back view of the balloon detachment tool in FIG. 1 as viewed in the III direction in FIG. 1, and FIG. 4 is a back view of a balloon detachment tool, which indicates a modification in which two cut portions are formed in the holding portion in FIG. 1.

Figure 5:
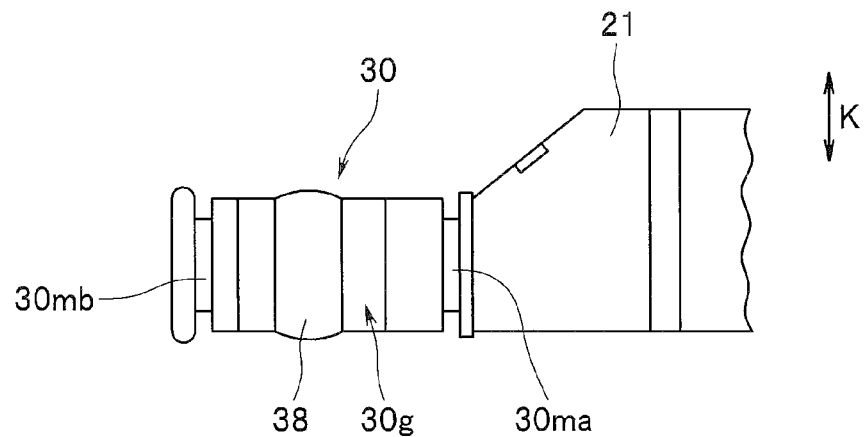
FIG. 5 is a diagram partially illustrating the distal-end side of an insertion portion of an ultrasound endoscope.
Figure 6:
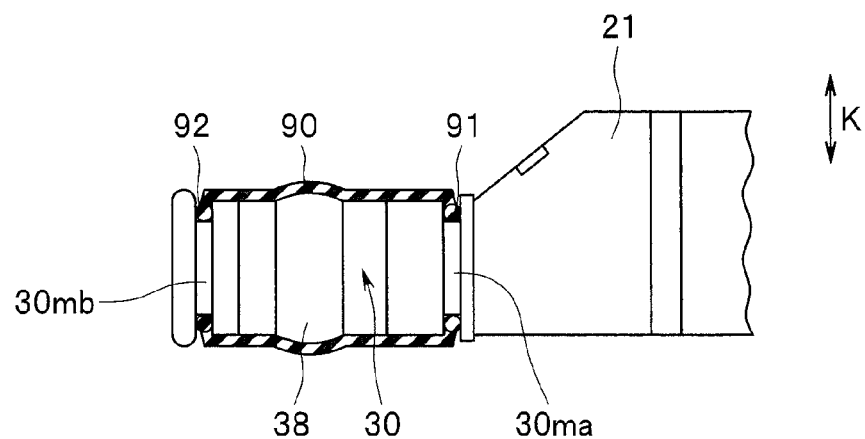
FIG. 6 is a diagram partially illustrating a state in which a balloon is attached to an outer periphery of the ultrasound transducer unit in FIG. 5.
Figure 7:
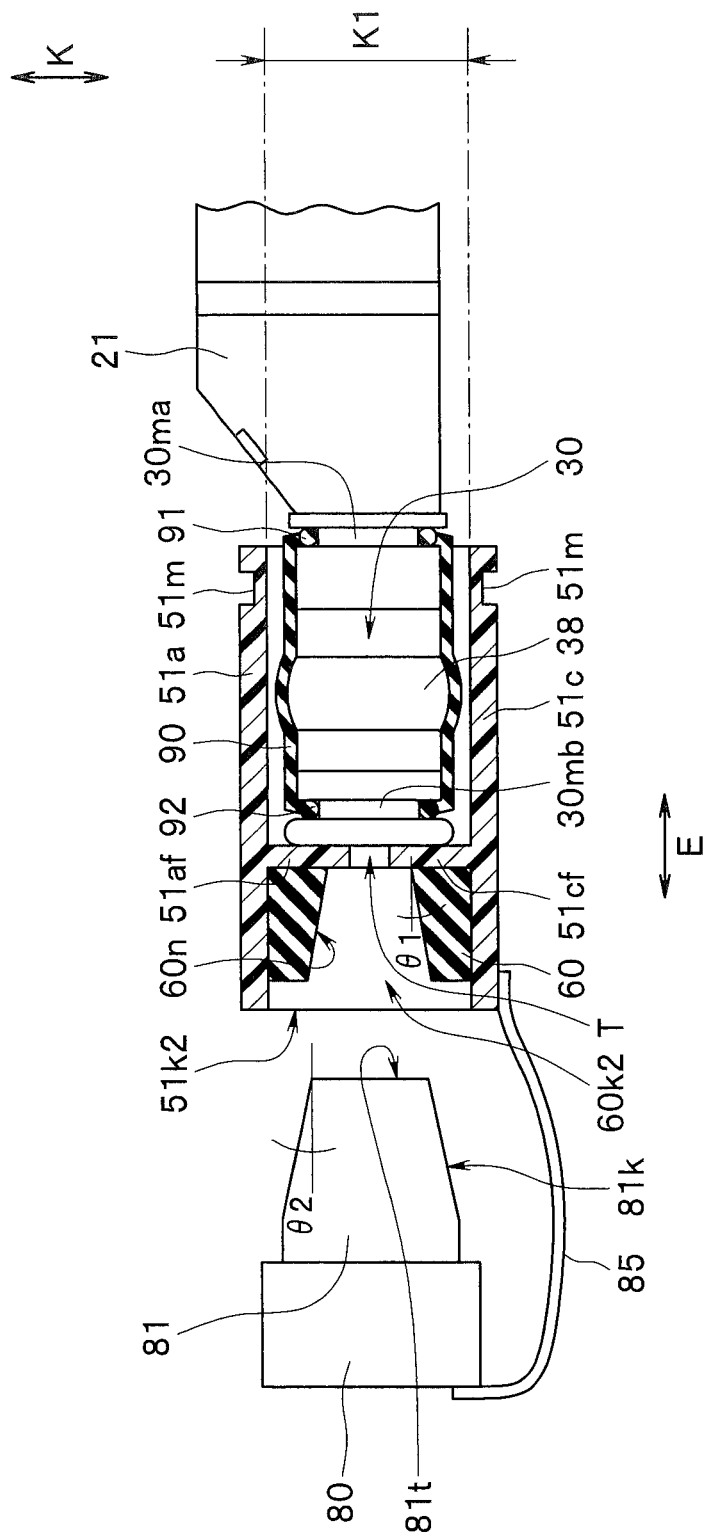
FIG. 7 is a partial cross-sectional diagram illustrating a state in which the ultrasound transducer unit in FIG. 6 is fitted in the holding portion of the balloon detachment tool in FIG. 1, together with a radial expansion portion.

Also, FIG. 5 is a diagram partially illustrating the distal-end side of an insertion portion of an ultrasound endoscope, FIG. 6 is a diagram partially illustrating a state in which a balloon is attached to an outer periphery of the ultrasound transducer unit in FIG. 5, and FIG. 7 is a partial cross-sectional diagram illustrating a state in which the ultrasound transducer unit in FIG. 6 is fitted in the holding portion of the balloon detachment tool in FIG. 1, together with a radial expansion portion.

Figure 8:
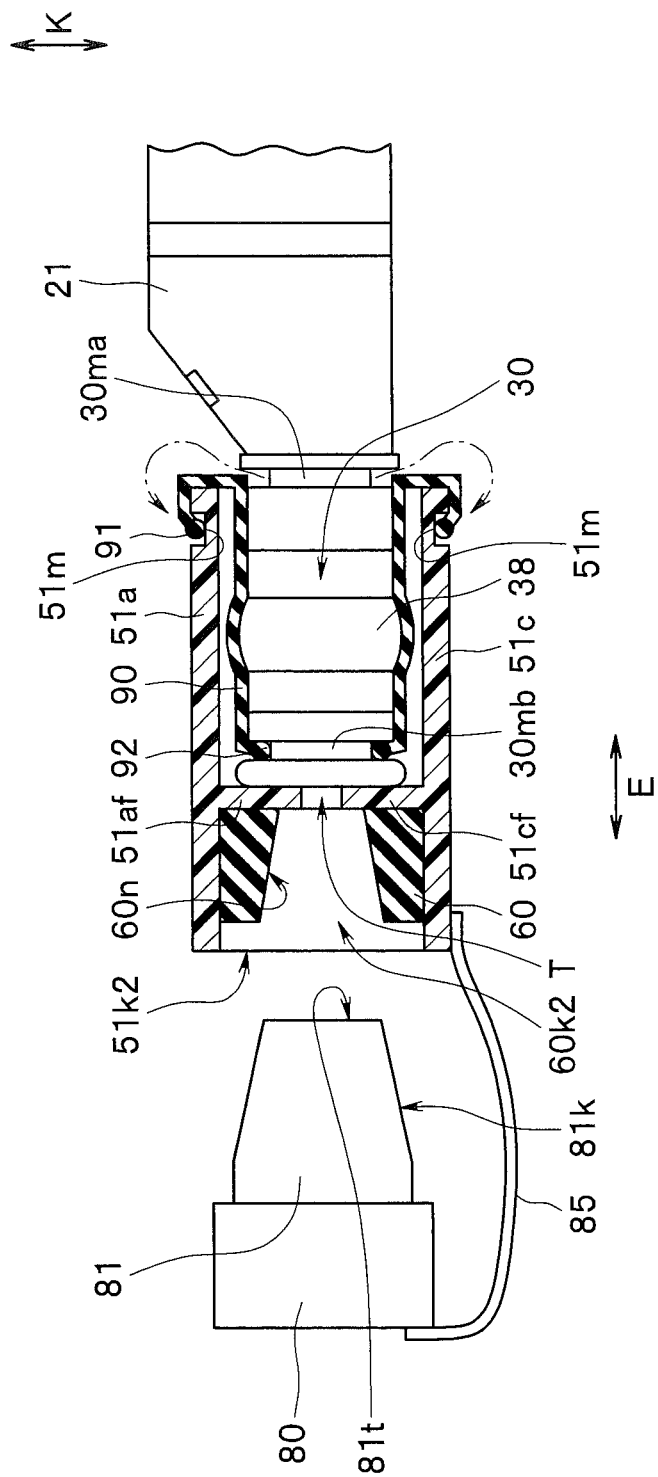
FIG. 8 is a partial cross-sectional diagram illustrating a state in which a balloon band on the one end side, engaged with a groove on the proximal-end side of the ultrasound transducer unit in FIG. 7, is moved to and engaged with a groove in the holding portion.
Figure 9:
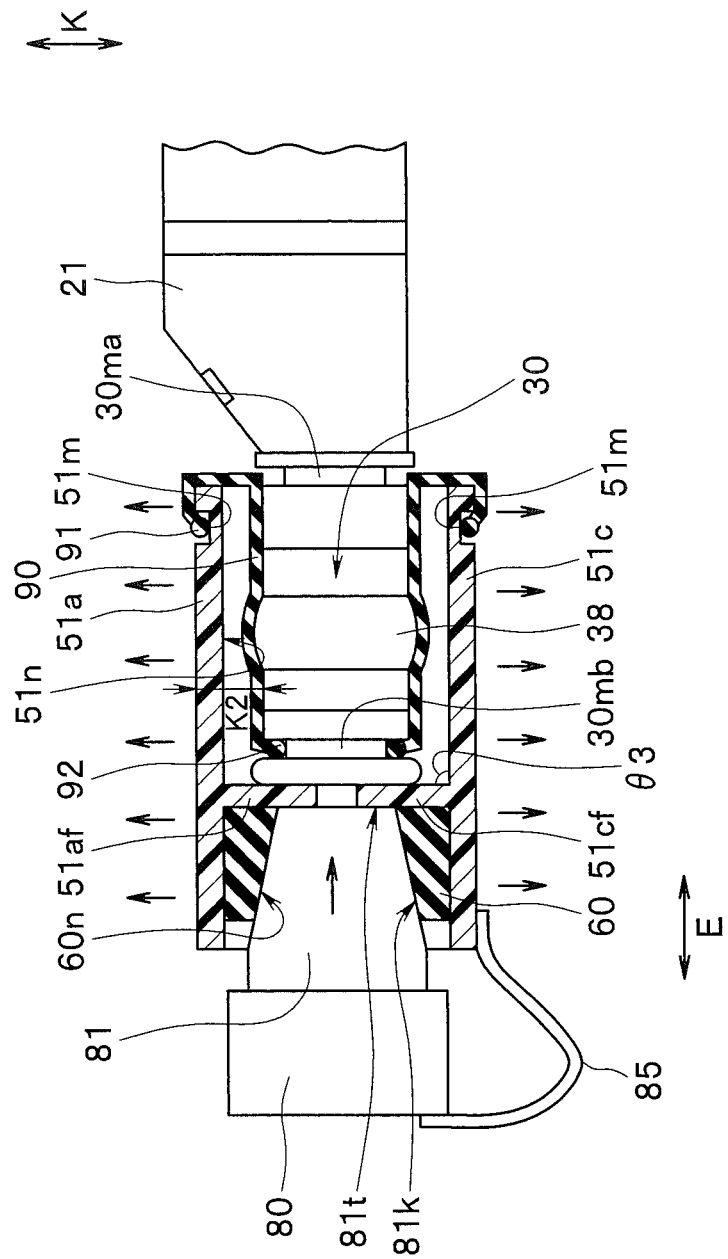
FIG. 9 is a partial cross-sectional diagram illustrating a state in which the radial expansion portion is fitted in the fitting portion in FIG. 8.

Furthermore, FIG. 8 is a partial cross-sectional diagram illustrating a state in which a balloon band on the one end side, engaged with a groove on the proximal-end side of the ultrasound transducer unit in FIG. 7, is moved to and engaged with a groove in the holding portion, and FIG. 9 is a partial cross-sectional diagram illustrating a state in which the radial expansion portion is fitted in the fitting portion in FIG. 8.

Figure 10:
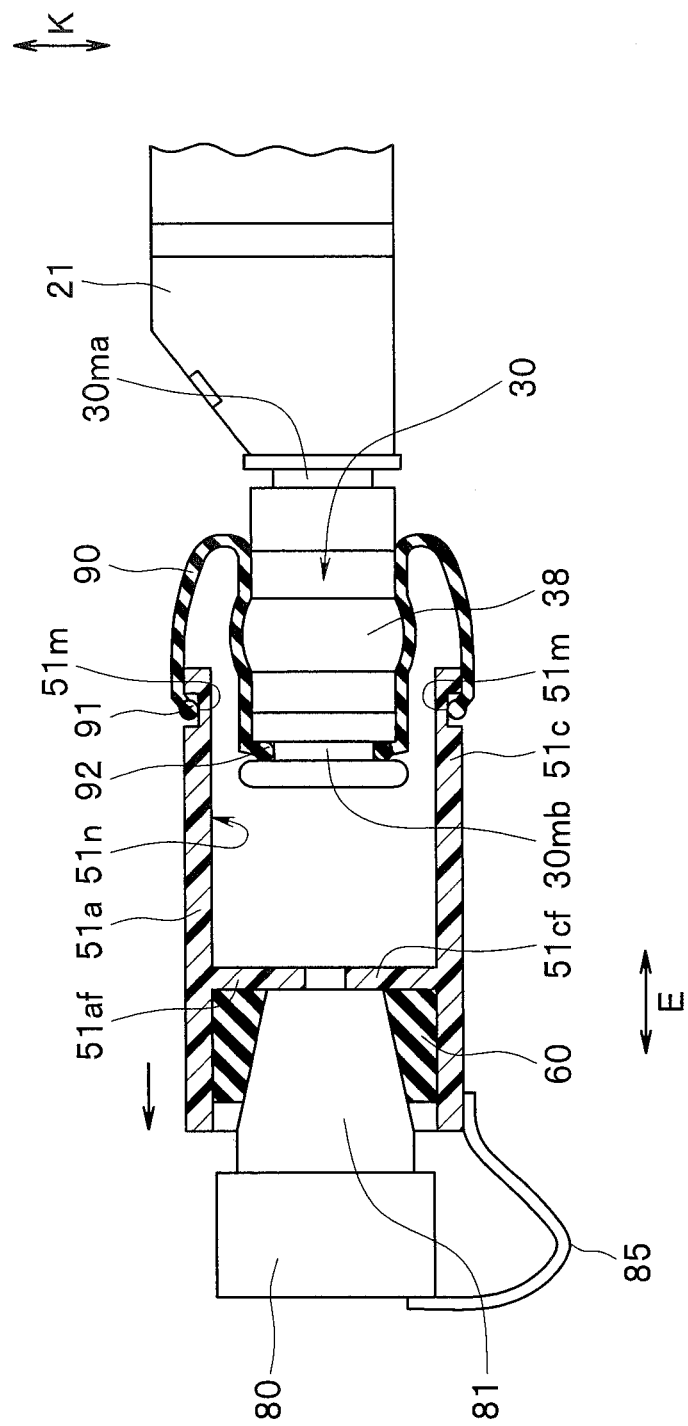
FIG. 10 is a partial cross-sectional diagram illustrating a state in which the holding portion in FIG. 9 is moved forward in an axial direction relative to the state in FIG. 9.
Figure 11:
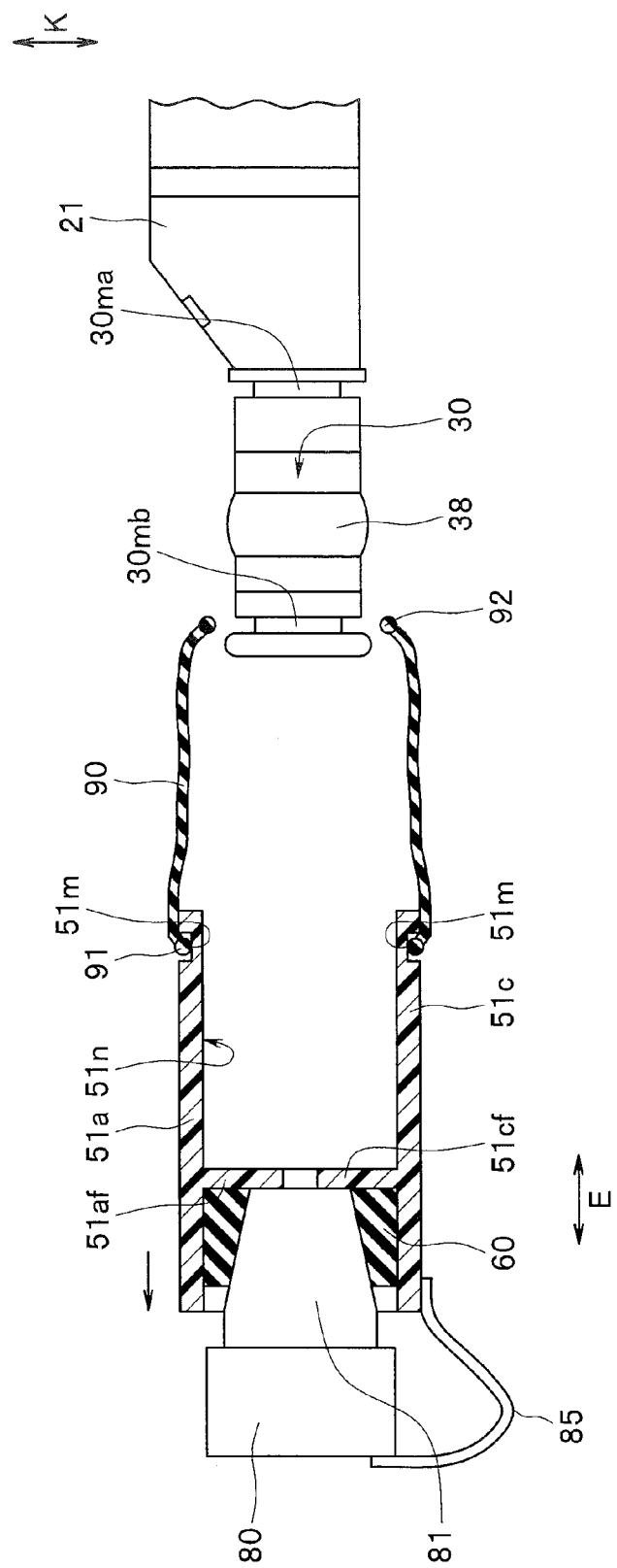
FIG. 11 is a partial cross-sectional diagram illustrating a state in which the holding portion in FIG. 10 is moved further forward in the axial direction relative to the state in FIG. 10 and the balloon is detached from the outer periphery of the ultrasound transducer unit.

Also, FIG. 10 is a partial cross-sectional diagram illustrating a state in which the holding portion in FIG. 9 is moved forward in an axial direction relative to the state in FIG. 9, and FIG. 11 is a partial cross-sectional diagram illustrating a state in which the holding portion in FIG. 10 is moved further forward in the axial direction relative to the state in FIG. 10 and the balloon is detached from the outer periphery of the ultrasound transducer unit.

As illustrated in FIG. 1, a balloon detachment tool 50 includes a holding portion 51. Note that the balloon detachment tool may be either a disposable one or a reusable one.

As illustrated in FIG. 7, the holding portion 51 is formed in a cylindrical shape having an inner diameter K1 that allows an ultrasound transducer unit 30 at a distal end of an insertion portion 2 of an ultrasound endoscope 1 (see FIG. 14 for both) to inserted/extracted to/from the inside thereof in a loose-fit state.

Also, as illustrated in FIG. 1, the holding portion 51 includes a first opening 51k1 at one end 51p in an axial direction E and a second opening 51k2 at the other end 51q in the axial direction E.

Note that the inner diameter K1 may be a diameter that is slightly larger than an outer diameter of the ultrasound transducer unit 30. Also, the holding portion 51 includes, e.g., a resin.

Also, as illustrated in FIGS. 1 and 3, in the holding portion 51, four cut portions S that each cut the holding portion 51 from the one end 51p to the other end 51q along the axial direction E, are formed at set intervals along a circumferential direction C of the holding portion 51.

In other words, as illustrated in FIGS. 1 and 3, the holding portion 51 includes four members 51a, 51b, 51c and 51d having shapes that are identical to one another, the shapes being rough partial arc shapes separated by the four cut portions S and also plate-like shapes that are elongated along the axial direction E.

Note that the number of cut portions S is not limited to four and may be any of one to three, or five or more.

Also, as illustrated in FIG. 4, where the number of cut portions is two, the holding portion 51 includes two members 51e and 51f having shapes that are identical to each other, the shapes being rough semicircular shapes separated by two cut portions S and also shapes that are elongated plate-like shapes along the axial direction E.

Also, as illustrated in FIGS. 1 and 7 to 11, in an outer periphery 51g of the holding portion 51, a groove 51m that allows a balloon band 91 to be engaged therein, the balloon band 91 being provided at an end that is an end of a balloon 90, the end being removed from an outer periphery 30g of an ultrasound transducer unit 30 (see FIG. 6 for both), is formed at a position a set distance E1 away toward the other end 51q side from the one end 51p in the axial direction E.

In other words, the groove 51m is formed in each of the outer periphery of the members 51a to 51d. Note that in the configuration illustrated in FIG. 4, the groove 51m is formed at a position the set distance E1 away from one end 51p of an outer periphery of each of the members 51e and 51f.

Figure 14:
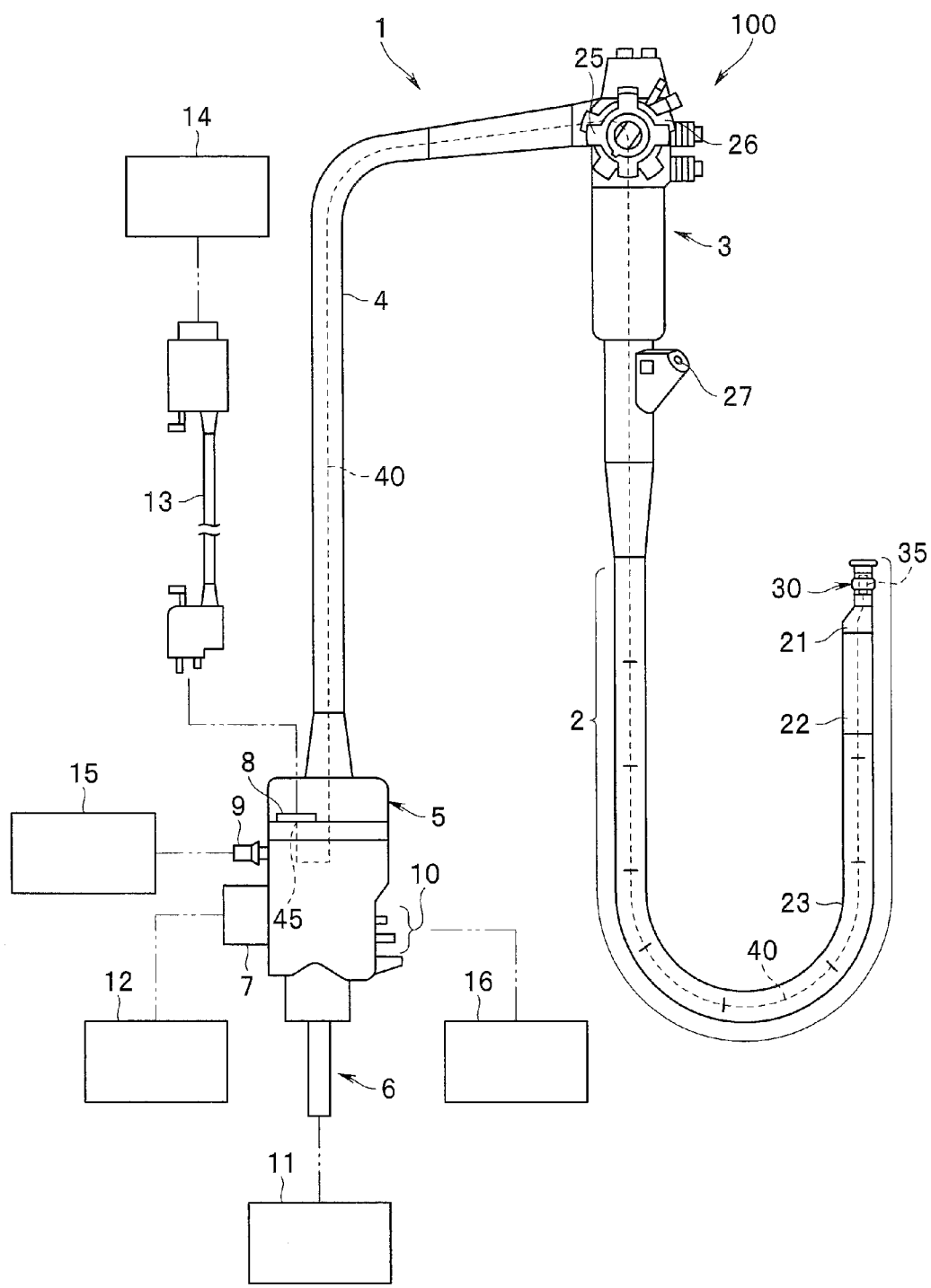
FIG. 14 is a diagram illustrating an ultrasound endoscope apparatus including an ultrasound endoscope including the ultrasound transducer unit in FIG. 5.

Here, as illustrated in FIG. 6, the balloon 90 is attached to the outer periphery 30g of the ultrasound transducer unit 30 provided on the distal-end side of a distal end portion 21 of the insertion portion 2 (see FIG. 14).

Note that as an example, the ultrasound transducer unit 30 may be an electronic radial-type ultrasound transducer unit including an ultrasound transducer 35 (see FIG. 14) that can transmit/receive ultrasound in a 360° degree radius in a non-illustrated housing, and an acoustic lens 38 on an outer surface circumferentially exposed from the housing. The ultrasound transducer unit 30 is not limited to an electronic radial-type one.

Also, as illustrated in FIGS. 5 and 6, the balloon 90 is attached to the outer periphery 30g of the ultrasound transducer unit 30 so as to cover the acoustic lens 38 by engaging the balloon band 91 provided at one end of the balloon 90 in a groove 30ma provided on the proximal-end side of the ultrasound transducer unit 30 and engaging a balloon band 92 provided at the other end of the balloon 90 in a groove 30*mb* provided on the distal-end side of the ultrasound transducer unit 30 in the distal end portion 21.

Also, as illustrated in FIG. 1, on the second opening 51*k*2 side in an inner portion of the holding portion 51, a fitting portion 60 that radially contracts an inner peripheral face 51*n* of the holding portion 51 from the other end 51*q* toward the one end 51*p* is positioned in such a manner that an outer peripheral face of the fitting portion 60 are in abutment with inner peripheral faces 51*n* of the respective members 51*a* to 51*d*.

As illustrated in FIG. 2, the fitting portion 60 is formed in a cylindrical shape, and includes a member that is separate from the holding portion 51 and can radially expand in a radial direction K of the holding portion 51. Note that as an example, the member included in the fitting portion 60 may be an elastic member or a fabric member such as Japanese paper or felt.

Furthermore, as illustrated in FIG. 1, the fitting portion 60 is provided so as to be fitted into the second opening 51*k*2 side of the holding portion 51. Also, as illustrated in FIG. 2, the fitting portion 60 includes an inner peripheral face 60*n* formed at an inclined surface of the fitting portion 60, which radially contracts toward one end 60*p* from the other end 60*q*, and at the one end 60*p*, an opening 60*k*1 having a diameter that is smaller than that of the opening 60*k*2 at the other end 60*q* is formed.

Also, as illustrated in FIGS. 1 and 2, on the inner peripheral face 51*n* of the holding portion 51, that is, on the respective inner peripheral faces 51*n* of the respective members 51*a* to 51*d*, respective abutment portions 51*af*, 51*bf*, 51*cf* and 51*df* that project inward in the radial direction K from the inner peripheral face 51*n* and against which an end portion on the one end 60*p* side of the fitting portion 60 abuts are formed on the one end 51*p* side relative to the one end 60*p* of the fitting portion 60 in the axial direction E.

Note that if the holding portion 51 includes the members 51*e* and 51*f* as illustrated in FIG. 4, on the respective inner peripheral faces 51*n* of the respective members 51*e* and 51*f*, abutment portions 51*ef* and 51*ff* that project inward in the radial direction K from the inner peripheral faces 51*n* and against which the end portion on the one end 60*p* side of the fitting portion 60 abuts are formed on the one end 51*p* side relative to the one end 60*p* of the fitting portion 60 in the axial direction E.

Also, as illustrated in FIGS. 3 and 4, at a rough center in the radial direction K of the abutment portions 51*af* to 51*df* or the abutment portions 51*ef* and 55*ff*, a through hole T extending in the axial direction E is formed, and the through hole T communicates with the opening 60*k*1. In other words, an inner portion of the fitting portion 60 and the inner portion on the proximal-end side relative to the abutment portions 51*af* to 51*df* of the holding portion 51 communicate with each other via the through hole T and the opening 60*k*1.

Furthermore, as illustrated in FIGS. 7 to 11, a fit-in portion 81 of a radial expansion portion 80 can be fitted to the inside of the fitting portion 60 via the second opening 51*k*2 and the opening 60*k*2.

The fit-in portion 81 of the radial expansion portion 80 includes an outer peripheral face 81*k* whose diameter is at least partially larger than an inner diameter of the fitting portion 60, and an abutting surface 81*t* that abuts against the abutment portions 51*af* to 51*df* or the abutment portions 51*ef* and 51*ff*.

An outer peripheral face 81*k* of the radial expansion portion 80 is formed as a tapered surface having an inclination angle θ2, which is different from an inclination angle θ1 of the inner peripheral face 60*n* of the fitting portion 60 as illustrated in FIG. 7.

As illustrated in FIG. 9, the radial expansion portion 80 has a function that upon the radial expansion portion 80 being fitted in the fitting portion 60, radially expands the fitting portion 60 outward in the radial direction K, thereby radially expanding the holding portion 51 outward in the radial direction K, and the radial expansion portion 80 is secured to a distal end of the outer periphery 51*g* of the holding portion 51 via, e.g., a strap 85 to prevent it from falling off. Note that the radial expansion portion 80 may be replaced by, e.g., a finger of a worker.

Next, a method for detaching the balloon 90 attached to the outer periphery 30*g* of the ultrasound transducer unit 30 as illustrated in FIG. 6 using the above-described balloon detachment tool 50 will be described.

First, as illustrated in FIG. 7, a worker fits the ultrasound transducer unit 30 into the holding portion 51 via the first opening 51*k*1 until the distal end abuts against the respective abutment portions 51*af* to 51*df* or 51*ef* and 51*ff*.

Subsequently, as illustrated in FIG. 8, the worker moves the balloon band 91 of the balloon 90, which is engaged in the groove 30*ma*, to the groove 51*m* of the outer periphery 51*g* of the holding portion 51 and engages the balloon band 91 in the groove 51*m* using, e.g., tweezers or fingers as indicated by the alternate long and short dash lines.

Here, the inner diameter K1 is slightly larger than the outer diameter of the ultrasound transducer unit 30, facilitating the work of moving the balloon band 91 from the groove 30*ma* to the groove 51*m*.

Also, here, an outer periphery of the aforementioned acoustic lens 38 is covered by the holding portion 51, whereby the acoustic lens 38 is prevented from being damaged as a result of the work of moving the balloon band 91.

Next, as illustrated in FIG. 9, the worker fits the fit-in portion 81 of the radial expansion portion 80 into the fitting portion 60 via the second opening 51*k*2 and the opening 60*k*2 until the abutting surface 81*t* abuts against the respective abutment portions 51*af* to 51*df* or 51*ef* and 51*ff*.

Here, immediately after the fit-in portion 81 is fitted in the fitting portion 60, the fitting portion 60 radially expands outward in the radial direction K because of the difference in inclination angle between the inner peripheral face 60*n* and the outer peripheral face 81*k* and the outer diameter of the fit-in portion 81 that is larger than the inner diameter of the fitting portion 60, and thus the distal-end side of the holding portion 51 also radially expands outward in the radial direction K, while the proximal-end side of the holding portion 51 radially contracts inward in the radial direction K.

However, until the abutting surface 81*t* abuts against the respective abutment portions 51*af* to 51*df* or the abutment portions 51*ef* and 51*ff*, a force of radial outward expansion in the radial direction K is exerted also on the first opening 51*k*1 because of the difference in inclination angle between the inner peripheral face 60*n* and the outer peripheral face 81*k* and the outer diameter of the fit-in portion 81 that is larger than the inner diameter of the fitting portion 60, whereby the proximal-end side of the holding portion 51 also radially expands in the radial direction K.

Here, an angle θ3 formed between the inner peripheral face 51*n* and each of the abutment portions 51*af* to 51*df* or 51*ef* and 51*ff* is 80° to 100°, preferably 85° to 95°, more preferably 90°.

Also, since the abutting surface 81*t* abuts against the respective abutment portions 51*af* to 51*df* or 51*ef* and 51*ff*, the ultrasound transducer unit 30 is prevented from being damaged by the abutting surface 81*t* abutting against the ultrasound transducer unit 30 as a result of the fitting-in of the fit-in portion 81.

As a result, a gap K2 that is larger than that before the fit-in portion 81 is fitted in the fitting portion 60 is formed between the inner peripheral face 51*n* of the holding portion 51 and the outer periphery 30*g* of the ultrasound transducer unit 30.

Subsequently, as illustrated in FIG. 10, the worker pulls the balloon detachment tool 50 forward with the fit-in portion 81 kept in the fitting portion 60.

As a result, because of the balloon band 91 being engaged in the groove 51*m*, the balloon 90 start being removed from the outer periphery 30*g* of the ultrasound transducer unit 30 along with the forward movement of the balloon detachment tool 50. Here, the large gap K2 prevents the inner peripheral face 51*n* from coming into contact with the acoustic lens 38.

Lastly, as illustrated in FIG. 11, the worker pulls the balloon detachment tool 50 further forward relative to the state in FIG. 10, whereby the balloon 90 is removed from the outer periphery 30*g* of the ultrasound transducer unit 30 and the balloon band 92 engaged in the groove 30*mb* comes off from the groove 30*mb*. Consequently, the balloon 90 is detached from the outer periphery 30*g* of the ultrasound transducer unit 30.

As described above, in the present embodiment, it has been indicated that the balloon detachment tool 50 including: the holding portion 51; the fitting portion 60 fitted in the inner portion on the distal-end side of the holding portion 51; the abutment portions 51*af* to 51*df* or 51*ef* and 51*ff* against which the one end 60*p* of the fitting portion 60 abuts; and the groove 51*m* formed in the outer periphery of the holding portion 51, the groove 51*m* allowing the balloon band 91 moved from the groove 30*ma* to be engaged therein.

Also, it has been indicated that upon the fit-in portion 81 being fitted in the fitting portion 60 until the abutting surface 81*t* of the fit-in portion 81 of the radial expansion portion 80 abuts against the respective abutment portions 51*af* to 51*df* or 51*ef* and 51*ff*, the fitting portion 60 radially expands outward in the radial direction K, whereby the holding portion 51 radially expands outward in the radial direction K and the large gap K2 is formed between the inner peripheral face 51*n* of the holding portion 51 and the outer periphery 30*g* of the ultrasound transducer unit 30.

Furthermore, it has been indicated that upon the balloon detachment tool 50 being pulled out forward with the holding portion 51 radially expanded outward in the radial direction K and the balloon band 91 engaged in the groove 51*m*, the balloon 90 comes off from the outer periphery 30*g* of the ultrasound transducer unit 30.

Accordingly, the balloon 90 is removed by pulling the balloon detachment tool 50 out forward after the holding portion 51 is radially expanded outward in the radial direction K by fitting the fit-in portion 81 into the fitting portion 60, and thus, when the balloon detachment tool 50 is moved forward, the work of extracting the balloon detachment tool 50 can be performed with good workability because of the gap K2 in addition to prevention of the inner peripheral face 51*n* from coming into contact with the acoustic lens 38.

Therefore, as opposed to the conventional techniques, the acoustic lens 38 is prevented from being damaged in detaching work using a tool.

Furthermore, as illustrated in FIG. 7, in a state in which the ultrasound transducer unit 30 is fitted in the holding portion 51, the work of moving the balloon band 91 from the groove 30*ma* to the groove 51*m* can easily be performed because the inner diameter K1 of the inner peripheral face 51*n* is slightly larger than that of the outer periphery 30*g* of the ultrasound transducer unit 30, and during the movement work, the acoustic lens 38 is prevented from being damaged because the outer periphery of the acoustic lens 38 is covered by the holding portion 51.

According to the above, a balloon detachment tool 50 that enables easy detachment of a balloon 90 from an outer periphery 30*g* of an ultrasound transducer unit 30 without an acoustic lens 38 being damaged can be provided.

Figure 12:
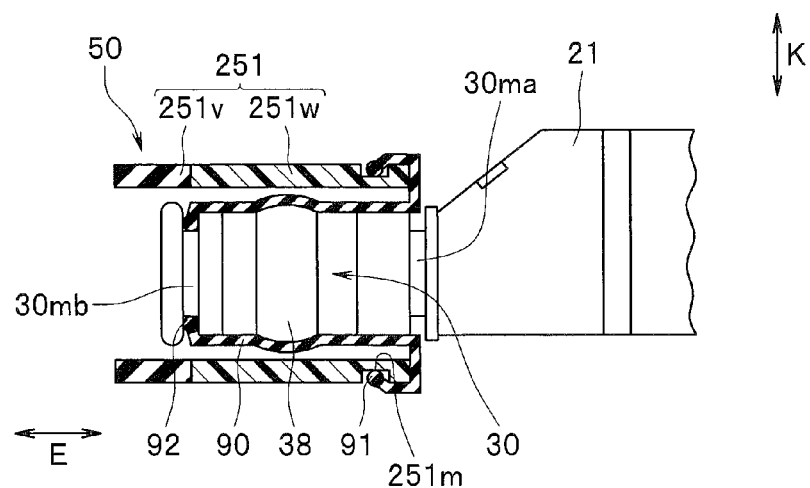
FIG. 12 is a partial cross-sectional diagram illustrating a modification in which the balloon detachment tool in FIG. 1 includes a holding portion whose distal end-side part includes an elastic member, in a state in which an ultrasound transducer unit is fitted in the holding portion.
Figure 13:
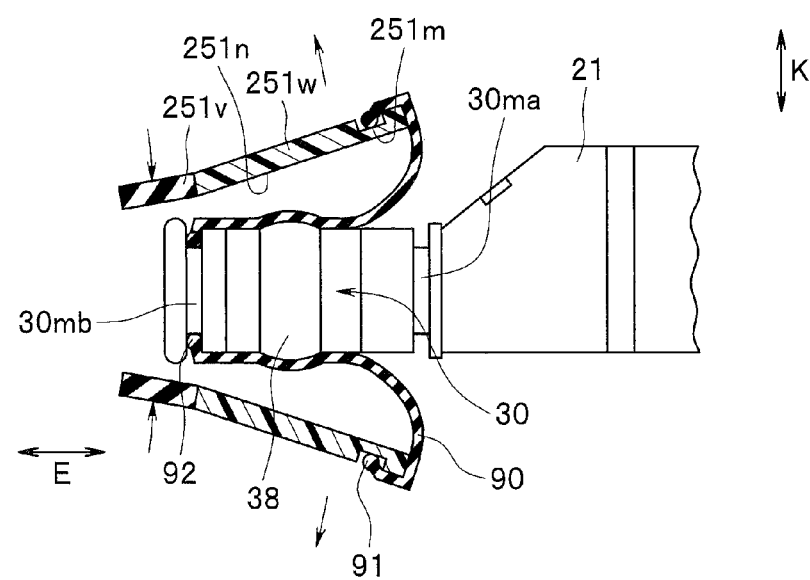
FIG. 13 is a partial cross-sectional diagram illustrating a state in which the distal end-side part of the holding portion in FIG. 12 is radially contracted and the proximal-end side of the holding portion is radially expanded.

A modification will be indicated below with reference to FIGS. 12 and 13. FIG. 12 is a partial cross-sectional diagram illustrating a modification in which the balloon detachment tool in FIG. 1 includes a holding portion whose distal end-side part includes an elastic member, in a state in which an ultrasound transducer unit is fitted in the holding portion, and FIG. 13 is a partial cross-sectional diagram illustrating a state in which the distal end-side part of the holding portion in FIG. 12 is radially contracted and the proximal-end side of the holding portion is radially expanded.

As illustrated in FIG. 12, in the present embodiment, a balloon detachment tool 50 may include a cylindrical holding portion 251 alone.

The holding portion 251 includes including a distal end-side part 251*v* including an elastic member that is elastically deformable, and another part 251*w* including, e.g., a resin.

Note that a groove 251*m* having a function that is the same as that of the above-described groove 51*m* is formed at a position a set distance E1 away from one end of the holding portion 251 in an axial direction E as described above in an outer periphery of the part 251*w*. Therefore, a balloon band 91 removed from a groove 30*ma* is engaged in the groove 251*m*.

Also, although not illustrated, non-illustrated slits are formed along the axial direction E in a part of the outer periphery of the part 251*w* of the holding portion 251.

In order to detach a balloon 90 from an outer periphery 30*g* of an ultrasound transducer unit 30 using such holding portion 251, first, as illustrated in FIG. 12, the ultrasound transducer unit 30 is fitted in the holding portion 251, and then, a balloon band 91 engaged in a groove 30*ma* is moved to and engaged in the groove 251*m*.

Here, since an outer periphery of an acoustic lens 38 is covered by the holding portion 251, the acoustic lens 38 is prevented from being damaged by the work of moving the balloon band 91.

Next, as illustrated in FIG. 13, a worker radially contracts the distal end-side part 251*v* inward in a radial direction K, which includes an elastic member, via, e.g., fingers.

As a result, the proximal-end side of the part 251*w* radially expands largely outward in the radial direction K because of the slits. In other words, the holding portion 251 is turned into a chevron shape. Subsequently, an inner peripheral face 251*n* of the holding portion 251 is largely spaced from the outer periphery 30*g* of the ultrasound transducer unit 30.

Lastly, the worker pulls the holding portion 251 out forward in this state. As a result, as in the present embodiment, the balloon 90 is detached from the outer periphery 30*g* of the ultrasound transducer unit 30.

Such configuration as above enables prevention of an acoustic lens 38 from being damaged as a result of the inner peripheral face 251*n* coming into contact with the acoustic lens 38 during the work of removing a balloon 90 and also enables the extraction work to be performed easily as in the present embodiment described above.

Note that although the above present embodiment has been described in terms of a case where the balloon detachment tool 50 is used to detach a balloon 90 from an outer periphery 30g of an ultrasound transducer unit 30, the present invention is not limited to this case, and the balloon detachment tool 50 may be used to attach a balloon 90 to an outer periphery 30g of an ultrasound transducer unit 30.

More specifically, a balloon band 91 is engaged in the groove 51m with a balloon band 92 engaged in the groove 30mb, and then, the fit-in portion 81 is fitted into the fitting portion 60, whereby the holding portion 51 radially expands outward in the radial direction K, and the ultrasound transducer unit 30 is fitted into the holding portion 51 via the first opening 51k1.

Subsequently, the fit-in portion 81 is extracted from the fitting portion 60 and the work of moving the balloon band 91 from the groove 51m to the groove 30ma and engaging the balloon band 91 in the groove 30ma is performed with the holding portion 51 radially contracted inward in the radial direction K, enabling the balloon 90 to be easily attached to the outer periphery 30g of the ultrasound transducer unit 30 as with the conventional techniques.

Note that the above-described ultrasound transducer unit 30 is used in, for example, an ultrasound endoscope 1.

FIG. 14 is a diagram illustrating an ultrasound endoscope apparatus including an ultrasound endoscope including the ultrasound transducer unit in FIG. 5.

As illustrated in FIG. 14, an ultrasound endoscope apparatus 100 includes a main part including an ultrasound endoscope 1, a light source apparatus 11, a video processor 12, an ultrasound observation apparatus 14, a suction pump 15 and a water feeding tank 16.

The ultrasound endoscope 1 includes a main part including an elongated insertion portion 2 to be inserted to the inside of a body, an operation portion 3 that is provided at a proximal end of the insertion portion 2 and doubles as a grasping portion, a universal cord 4 that has flexibility and extends from the operation portion 3, and an endoscope connector 5 provided at an extension end of the universal cord 4.

In the endoscope connector 5, a light source connector 6, an electric connector 7, an ultrasound connector 8, a suction fitting 9 and an air/water feeding fitting 10 are provided.

The light source apparatus 11 that supplies illuminating light is attachable/detachable to/from the light source connector 6. Also, the video processor 12 that performs, e.g., various signal processing via a non-illustrated signal cable is attachable/detachable to/from the electric connector 7.

Furthermore, the ultrasound observation apparatus 14 is attachable/detachable to/from the ultrasound connector 8 with a connector 45 electrically connected thereto, the connector 45 being provided on the proximal-end side of an ultrasound transducer cable 40 extending from the ultrasound transducer 35 in the ultrasound transducer unit 30, via an ultrasound cable 13.

Also, the suction pump 15 is attachable/detachable to/from the suction fitting 9 via a non-illustrated suction tube. Furthermore, the water feeding tank 16 is attachable/detachable to/from the air/water feeding fitting 10 via a non-illustrated air/water feeding tube.

The ultrasound observation apparatus 14 controls various operation of the ultrasound endoscope 1, and for example, controls driving of the ultrasound transducer 35, and performs operation to generate a video signal by performing signal processing of an electric signal acquired by the control of the driving of the ultrasound transducer 35.

Note that the video signal generated by the ultrasound observation apparatus 14 is outputted to a non-illustrated display apparatus. As a result, an ultrasound image is displayed on a screen of the display apparatus that has received the video signal.

The insertion portion 2 of the ultrasound endoscope 1 includes a distal end portion 21, a bending portion 22 that is bendable, for example, upward/downward and leftward/rightward, and a flexible tube portion 23 that has a long length and flexibility which are provided consecutively in this order from the distal-end side. Note that the above-described ultrasound transducer unit 30 is positioned on the distal-end side of the distal end portion 21 and is fixed to the distal end portion 21.

At the operation portion 3, bending operation knobs 25 and 26 for performing an operation for bending the bending portion 22 are provided. Also, at a position on the insertion portion 2 side of the operation portion 3, a treatment instrument insertion port 27 through which a treatment instrument is introduced to the inside of a body via a non-illustrated treatment instrument insertion duct provided inside the insertion portion 2 and the operation portion 3 is provided.

The video processor 12 performs signal processing on an electric signal transmitted from a non-illustrated image pickup unit provided inside the distal end portion 21 to generate a standard video signal, and outputs the video signal to the non-illustrated display apparatus to display an endoscopic observation image on the screen of the display apparatus.

What is claimed is:
1. A balloon detachment tool comprising:
a cylindrical holding portion including a first opening on one end side in an axial direction, the first opening having an inner diameter that allows an ultrasound transducer unit in a distal end of an insertion portion of an ultrasound endoscope to be inserted and extracted, and a second opening on another end side in the axial direction;
a first balloon engagement groove formed in an outer periphery of the holding portion, the first balloon engagement groove being at a position a set distance away toward the other end side in the axial direction from the one end, the first balloon engagement groove being engageable with an end portion of the balloon which is removed from a second balloon engagement groove provided in an outer periphery of the ultrasound transducer unit;
a cut portion provided in the holding portion, the cut portion allowing the holding portion to radially expand in a radial direction; and
an abutment portion provided on an inner peripheral face of the holding portion and on the second opening side relative to the first balloon engagement groove in the axial direction, the abutment portion positioning the first balloon engagement groove so that the first balloon engagement groove is located on a distal end side of the insertion portion of the ultrasound endoscope relative to the second balloon engagement groove when the abutment portion is brought into abutment with the distal end of the insertion portion of the ultrasound endoscope.

2. The balloon detachment tool according to claim 1, wherein the cut portion is a cut portion forming the holding portion from the one end to the other end in the axial direction.

3. The balloon detachment tool according to claim 1, further comprising a fitting portion positioned on the second opening side in an inner portion of the holding portion, the fitting portion radially contracting an inner peripheral face of the holding portion from the other end toward the one end and including a member that can radially expand in a radial direction of the holding portion.

4. The balloon detachment tool according to claim 3, wherein the fitting portion is formed in a cylindrical shape separately from the holding portion, and is provided so as to be fitted on the second opening side in the inner portion of the holding portion, and includes an inner peripheral face that radially contracts toward one end from another end of the fitting portion.

5. The balloon detachment tool according to claim 4, wherein a through hole extending in the axial direction is formed in the abutment portion, and the through hole communicates with an opening on the one end side of the fitting portion.

6. The balloon detachment tool according to claim 4, further comprising a radial expansion portion including an outer peripheral face whose diameter is at least partially larger than an inner diameter of the fitting portion, and an abutting surface that abuts against the abutment portion, the radial expansion portion being fitted into the fitting portion from an opening on the other end side of the fitting portion via the second opening, wherein when the radial expansion portion is fitted into the fitting portion, the radial expansion portion radially expands the fitting portion outward in the radial direction, so that the holding portion radially expands outward in the radial direction.

7. The balloon detachment tool according to claim 6, wherein the outer peripheral face of the radial expansion portion is formed as a tapered surface having an inclination angle that is different from an inclination angle of an inclined surface formed by the fitting portion in the inner peripheral face of the holding portion.

* * * * *